(12) United States Patent
Lin et al.

(10) Patent No.: US 11,872,069 B2
(45) Date of Patent: Jan. 16, 2024

(54) METHOD FOR PROVIDING FRACTURE-DETECTION TOOL

(71) Applicant: Chang Gung Memorial Hospital, Linkou, Taoyuan (TW)

(72) Inventors: Chi-Hung Lin, New Taipei (TW); Kevin C. Chung, Taoyuan (TW); Chang-Fu Kuo, Taoyuan (TW)

(73) Assignee: Chang Gung Memorial Hospital, Linkou, Taoyuan (TW)

( * ) Notice: Subject to any disclaimer, the term of this patent is extended or adjusted under 35 U.S.C. 154(b) by 294 days.

(21) Appl. No.: 17/195,405

(22) Filed: Mar. 8, 2021

(65) Prior Publication Data

US 2021/0275123 A1 Sep. 9, 2021

Related U.S. Application Data

(60) Provisional application No. 62/987,206, filed on Mar. 9, 2020.

(51) Int. Cl.

| | |
|---|---|
| *A61B 6/00* | (2006.01) |
| *G06N 3/08* | (2023.01) |
| *G16H 50/20* | (2018.01) |
| *G16H 30/20* | (2018.01) |
| *G06V 10/776* | (2022.01) |
| *G06N 3/04* | (2023.01) |
| *G06F 18/21* | (2023.01) |
| *G06V 10/764* | (2022.01) |
| *G06V 10/774* | (2022.01) |

(Continued)

(52) U.S. Cl.
CPC ............ *A61B 6/505* (2013.01); *G06F 18/217* (2023.01); *G06N 3/04* (2013.01); *G06N 3/08* (2013.01); *G06V 10/764* (2022.01); *G06V 10/774* (2022.01); *G06V 10/776* (2022.01); *G06V 10/778* (2022.01); *G06V 10/82* (2022.01); *G16H 30/20* (2018.01); *G16H 50/20* (2018.01)

(58) Field of Classification Search
CPC ........ A61B 6/505; G06F 18/217; G06N 3/08; G06V 10/776; G16H 30/20; G16H 50/20
See application file for complete search history.

(56) References Cited

U.S. PATENT DOCUMENTS

2020/0202168 A1* 6/2020 Mao ................. G01S 7/417

OTHER PUBLICATIONS

Lindsey et al. "Deep neural network improves fracture detection by clinicians", 2018, PNAS, vol. 115, No. 45, p. 11591-11596 (Year: 2018).*

(Continued)

*Primary Examiner* — Colin T. Sakamoto
*Assistant Examiner* — Andrew W Begeman
(74) *Attorney, Agent, or Firm* — Schwegman Lundberg & Woessner, P.A.

(57) ABSTRACT

A method includes a step of obtaining plural pieces of training data each of which includes a different radiographic image of a bone and each of which has a label indicating one of an overt fracture, an occult fracture and no fracture, a step of using the plural pieces of training data to pre-train a deep convolutional network (DCN) model to obtain a preliminary DCN model, a step of determining a subset of the plural pieces of training data by at least excluding any piece of training data that has a label indicating occult fracture, and a step of using the subset to train the preliminary DCN model to obtain a first DCN model.

13 Claims, 4 Drawing Sheets

(51) Int. Cl.
*G06V 10/778* (2022.01)
*G06V 10/82* (2022.01)

(56) References Cited

OTHER PUBLICATIONS

Ozkaya et al., "Evaluation of an artificial intelligence system for diagnosing scaphoid fracture on direct radiography", 2020, European Journal of Trauma and Emergency Surgery, vol. 48, p. 585-592 (Year: 2020).*

Laurent et al., "A Machine Learning Algorithm to Predict the Probability of (Occult) Posterior Malleolar Fractures Associated With Tibial Shaft Fractures to Guide "Malleolus First" Fixation", 2019, Journal of Orthopedic Trauma, vol. 34, No. 3 (Year: 2019).*

Johari et al., "Detection of vertical root fractures in intact and endodontically treated premolar teeth by designing a probabilistic neural network: an ex vivo study", 2016, Dentomaxilofacial Radiology, vol. 46 (Year: 2016).*

\* cited by examiner

METHOD FOR PROVIDING FRACTURE-DETECTION TOOL

CROSS-REFERENCE TO RELATED APPLICATION

This application claims priority of U.S. provisional Patent Application No. 62/987,206, filed on Mar. 9, 2020.

FIELD

The disclosure relates to a method, and more particularly to a method for providing fracture-detection tools.

BACKGROUND

Fractures of small bones include scaphoid fracture, which is a common type of carpal fracture, especially for young adult males. Overt small-bone fractures (e.g., overt scaphoid fractures) can be recognized from radiographs (e.g., hand radiographs) by experienced physicians, but it is difficult to confirm occult small-bone fractures (e.g., occult scaphoid fractures) from radiographs. Although computed tomography (CT) scan or magnetic resonance imaging (MRI) may be utilized to help confirm occult fractures, such approaches are expensive. An economical solution for detecting small-bone fractures is desired.

SUMMARY

Therefore, an object of the disclosure is to provide a method that facilitates detecting occult fractures from radiographs.

According to one aspect of the disclosure, the method includes a step of obtaining plural pieces of training data each of which includes a different radiographic image of a bone and has a label indicating one of an overt fracture, an occult fracture and no fracture, a steps of using the plural pieces of training data to pre-train a deep convolutional network (DCN) model to obtain a preliminary DCN model, a step of determining a subset of the plural pieces of training data by at least excluding any piece of training data that has a label indicating occult fracture, and a step of using the subset to train the preliminary DCN model to obtain a first DCN model, wherein the first DCN model, when receiving a piece of input data that includes a radiographic image of a bone under examination, outputs a score that indicates probability of overt fracture existing in the radiographic image of the bone under examination.

According to one aspect of the disclosure, the method further includes a step of determining multiple pieces of control data each of which includes a different radiographic image of a bone and, when being inputted to the first DCN model, enables the first DCN model to output a score indicating a low probability of overt fracture, and a step of using the multiple pieces of control data and said any piece of training data, whose label indicates occult fracture and which was excluded in the step of determining a subset, to train the first DCN model so as to obtain a second DCN model, wherein the second DCN model, when receiving another piece of input data that includes a radiographic image of a bone under examination, outputs a score indicating probability of occult fracture existing in the radiographic image.

BRIEF DESCRIPTION OF THE DRAWINGS

Other features and advantages of the disclosure will become apparent in the following detailed description of the embodiment(s) with reference to the accompanying drawings, of which.

DETAILED DESCRIPTION

Before the disclosure is described in greater detail, it should be noted that where considered appropriate, reference numerals or terminal portions of reference numerals have been repeated among the figures to indicate corresponding or analogous elements, which may optionally have similar characteristics.

Figure 1:
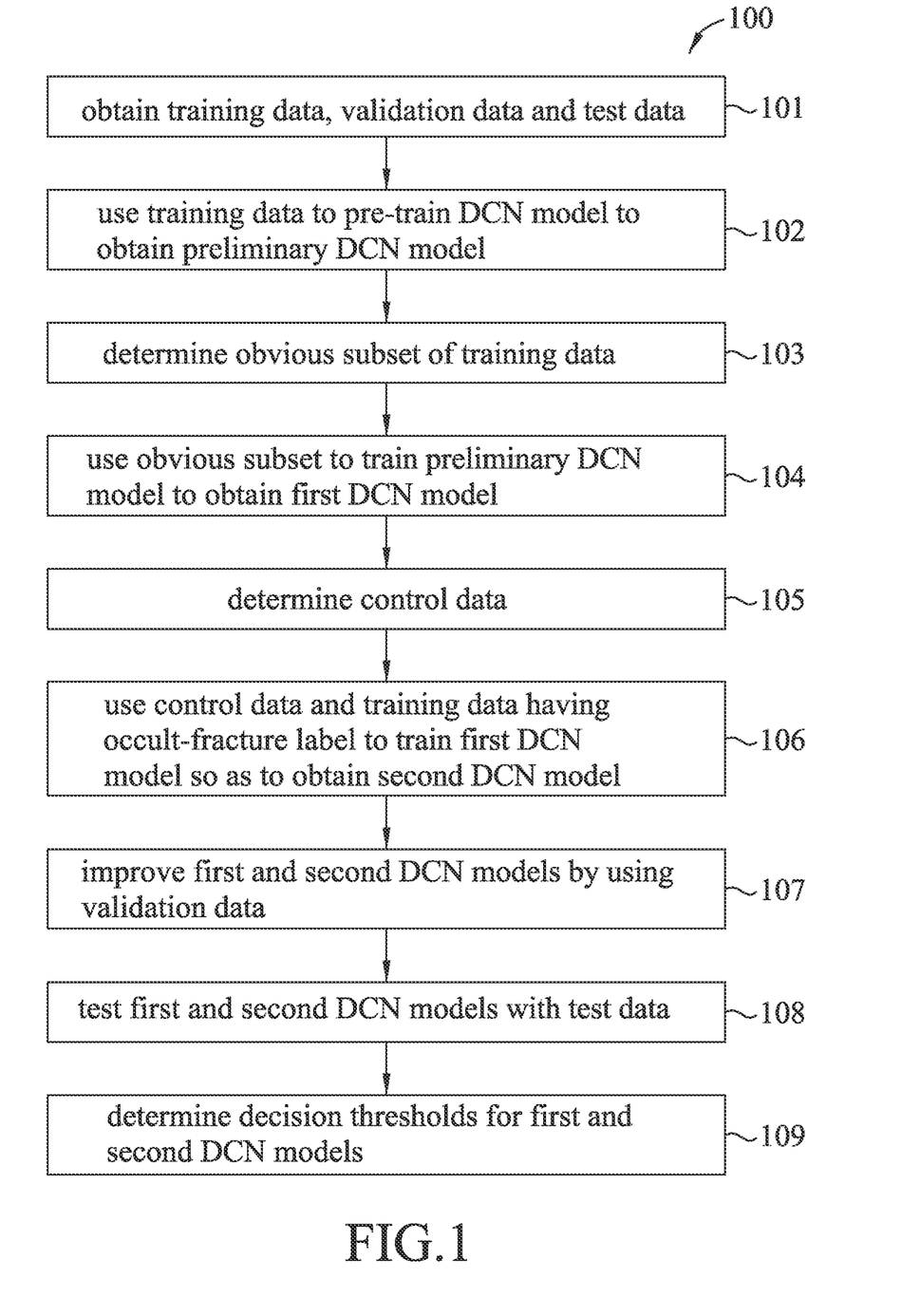
FIG. 1 is a flow chart that exemplarily illustrates a method for providing fracture-detection tools according to an embodiment of the disclosure.

FIG. 1 is a flow chart that exemplarily illustrates a method 100 for developing and providing fracture-detection tools based on deep convolutional network (DCN) technique according to an embodiment of the disclosure. The tools developed and provided by the method 100 can be utilized to detect overt and occult small-bone fractures, such as scaphoid fractures, based on radiographs (i.e., X-ray images). According to some embodiments, the method may be performed by a computing device that includes at least one processing device (e.g., a central processing unit (CPU), a graphic processing unit (GPU), etc.) and at least one memory device (e.g., random access memory (RAM), read only memory (ROM), programmable ROM (PROM), flash memory, etc). The processing device may be, for example, a personal computer (PC), a workstation or a server, but the disclosure is not limited thereto.

Referring to FIG. 1, the method 100 starts from Step 101, in which the computing device obtains plural pieces of training data, plural pieces of validation data and plural pieces of test data. Each piece of data among the plural pieces of training data, the plural pieces of validation data and the plural pieces of test data (i.e., each piece of training/validation/test data) includes a different radiographic image of a bone of interest (a small bone, such as a scaphoid, which is referred to as a relevant bone hereinafter), and has a label indicating one of an overt fracture, an occult fracture and no fracture with respect to the relevant bone.

Figure 2:
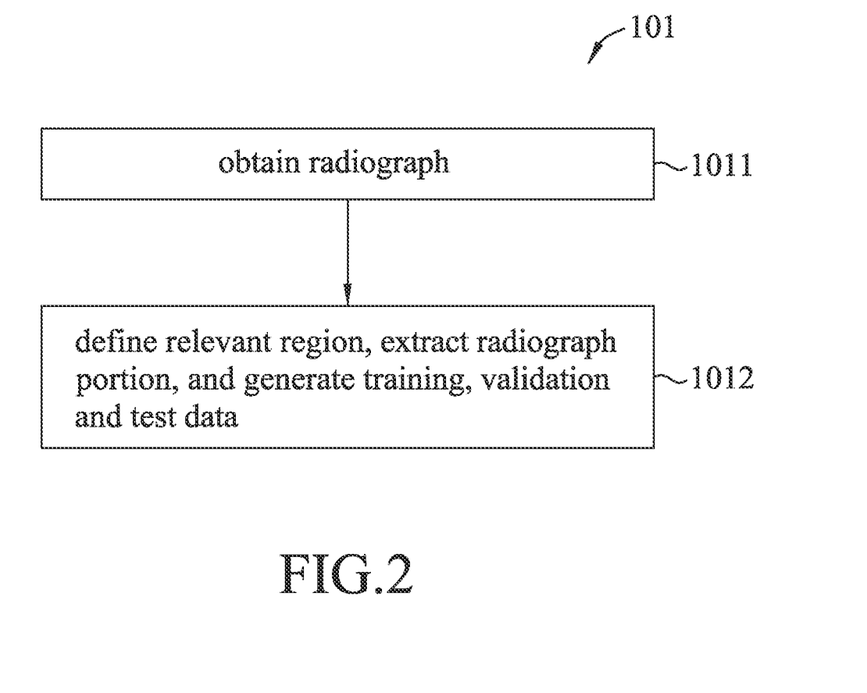
FIG. 2 is a flow chart that exemplarily illustrates sub-steps of Step 101 of FIG. 1 according to an embodiment of the disclosure.

According to some embodiments, Step 101 may include Sub-steps 1011 and 1012 that are shown in FIG. 2. Referring to FIG. 2, in Sub-step 1011, the computing device obtains a plurality of radiographs of the relevant bones of plural people, wherein fracture condition of the relevant bone in each of the radiographs has been confirmed as one of an overt fracture, an occult fracture and no fracture. In an embodiment that is to provide tools for detecting scaphoid fractures, the plurality of radiographs are each a posterior-anterior (PA) scaphoid view that includes no hardware (e.g., a screw, a plate, a wire, a pin, etc.) or external immobilization (e.g., a cast, a splint, etc.). According to some embodiments, the plurality of radiographs may be in Digital Imaging and Communications in Medicine (DICOM) format, and may be collected from institutions (e.g., hospitals or academic medical centers) located in different regions, or even different countries in order to reduce sampling bias. According to some embodiments, the plurality of radiographs thus collected may be randomly divided into three portions in accordance with a designated proportion, wherein a first portion among the three portions is used for training a DCN model and is referred to as a set of training radiographs, a second portion among the three portions is used for validation of the DCN model and is referred to as a set of validation radiographs, and a third portion among the three portions is used for testing the DCN model and is referred to as a set of test radiographs. In an embodiment, the proportion of the first, second and third portions is approximately 66:15:19, but the disclosure is not limited thereto. For each of all the radiographs collected from the institutions, the fracture condition (overt fracture, occult fracture or no fracture) of the relevant bone therein may be confirmed by a group of senior musculoskeletal radiologists, possibly with the help of confirmatory imaging such as repeat X-rays, computed tomography (CT) scans and/or magnetic resonance imaging (MRI).

Next, in Sub-step 1012, the computing device, for each of the plurality of radiographs (including the training radiographs, the validation radiographs and the test radiographs), analyzes the radiographs to define a region of interest (e.g., a scaphoid region, and referred to as a relevant region hereinafter) in the radiograph, extracts a portion of the radiograph that contains the relevant region, and generates a piece of data that corresponds to the radiograph, that includes the portion of the radiograph which serves as a radiographic image, and that has a label which is set based on which one of an overt fracture, an occult fracture and no fracture the radiograph (specifically, in the relevant region of the radiograph) is confirmed to show, wherein a piece of data thus generated that corresponds to a training radiograph is referred to as a piece of training data, a piece of data thus generated that corresponds to a validation radiograph is referred to as a piece of validation data, and a piece of data thus generated that corresponds to a test radiograph is referred to as a piece of test data. That is, in Sub-step 1012, plural pieces of training data, plural pieces of validation data and plural pieces of test data are generated based on the training radiographs, the validation radiographs and the test radiographs, respectively.

According to some embodiments, the plurality of radiographs, before being analyzed, may have had pixels thereof standardized by, for example, using a DICOM tag of 0x00280101 that relates to image depth, and may have been converted to RGB color scale with each pixel value being normalized to a value ranging from −1 to 1. According to some embodiments, the relevant region may be defined by using a dedicated recognition tool which is a Cascade Region-based Convolutional Neural Network (Cascade R-CNN) model that has been trained for locating the relevant bone (e.g., scaphoid) in a radiograph and generating a bounding box that separates a region of interest (ROI) (i.e., the relevant region) of the radiograph that includes the relevant bone from the remaining region of the radiograph not including the relevant bone. Said Cascade R-CNN model may be trained by using a training set of radiograph images (which may be DICOM images), in each of which bony landmarks that mark an outline of the relevant bone have been manually annotated using, for example, a LabelMe annotation tool (modified to be applied on radiograph images), and PyTorch and MMDetection packages.

Returning to FIG. 1, after the plural pieces of training data have been obtained in Step 101, the process goes to Step 102, in which the computing device uses the plural pieces of training data to pre-train a DCN model to initialize parameters of the DCN model, in order to obtain a preliminary DCN model. This pre-training or parameter-initialization process is efficient in reducing overfitting and speeding up a subsequent training process. In an embodiment, the DCN model is an existing EfficientNetB3 model, and the DCN model is to be trained by using a Tensorflow deep learning framework created by Google, but the disclosure is not limited thereto. Furthermore, in said embodiment, the DCN model is fine-tuned using an AdamW optimizer with an initial learning rate of $1e^{-5}$, a weight decay of $1e^{-6}$, and a batch size of 20, wherein the learning rate is reduced when a validation loss does not improve for six epochs, but the disclosure is not limited thereto.

In Step 103, the computing device determines a subset (referred to as obvious subset hereinafter) of the plural pieces of training data by at least excluding any piece of training data that has a label indicating occult fracture. According to some embodiments, the obvious subset may be obtained by further excluding any piece of training data that corresponds to a radiograph that is not a PA view (e.g., an oblique view or a lateral view), that has poor image quality (e.g., poor image detail, poor image contrast, or inappropriate film darkness), that shows a fracture that was older than four weeks and was healing or healed at the time the radiograph was taken, that includes the relevant bone having a doubtful fracture condition (e.g., lacking support of other confirmatory image(s) or involving contradicting radiology diagnoses), or that shows a chronic hand condition with bony change(s) around the relevant bone.

Next, in Step 104, the computing device uses the pieces of training data included in the obvious subset to train the preliminary DCN model to obtain a first DCN model that may serve as a base for a fraction-detection tool that is to be used for detecting overt fracture in the relevant bone in a radiograph. In an embodiment, this training process re-purposes the DCN model which is an existing EfficientNetB3 model to fracture detection of the relevant bone. In an embodiment, the training process is implemented according to transfer learning, and terminates when a model performance does not improve after 15 epochs. The first DCN model thus obtained, when receiving a piece of input data that corresponds to a radiograph including a relevant bone (e.g., scaphoid) under examination and that includes a radiographic image of the relevant bone under examination which is generated from the radiograph, outputs a score indicating probability of overt fracture existing in the radiographic image of the relevant bone under examination.

According to some embodiments, the first DCN model, when receiving the piece of input data, may further output a gradient-weighted class activation mapping (Grad-CAM) image that indicates a possible site of any fracture that is present in the radiographic image included in the piece of input data. The Grad-CAM image may be obtained based on outputted scores, gradients and last convolution layers of the first DCN model by utilizing the technique disclosed in an article entitled "Grad-cam: Visual explanations from deep networks via gradient-based localization" and authored by Ramprasaath R. Selvaraju et al., and image processing related to the Grad-CAM image may be implemented by utilizing Pydicom (e.g., version 1.4.1) and OpenCV (e.g., version 4.1) in Python (e.g., version 3.7), but the disclosure is not limited thereto.

In Step 105, the computing device determines multiple pieces of control data each of which includes a different radiographic image of the relevant bone and, when being inputted to the first DCN model, enables the first DCN model to output a score indicating a low probability of overt fracture. According to an embodiment, the multiple pieces of control data may be selected from among the pieces of training data included in the obvious subset. In an embodiment where the score outputted by the first DCN model is a value ranging from 0 to 1, a score lower than 0.2 is considered as a low probability, but the disclosure is not limited thereto.

Then, in Step 106, using the multiple pieces of control data determined in Step 105 and each piece of training data whose label indicates occult fracture and which was excluded in Step 103, the computing device trains the first DCN model, in order to obtain a second DCN model. The second DCN model is an advanced DCN model of the first DCN model that has been fine-tuned using the pieces of training data associated with occult fractures, such that sensitivity for detecting occult fractures is increased. The second DCN model may serve as a base for another fraction-detection tool that is to be used for detecting occult fracture in the relevant bone in a radiograph. The second DCN model, when receiving a piece of input data that corresponds to a radiograph including a relevant bone (e.g., scaphoid) under examination and that includes a radiographic image of the relevant bone under examination which is generated from the radiograph, outputs a score indicating probability of occult fracture existing in the radiographic image of the relevant bone under examination. According to an embodiment, the second DCN model, when receiving the piece of input data, may further output a gradient-weighted class activation mapping (Grad-CAM) image that indicates a possible site of any fracture that is present in the radiographic image included in the piece of input data.

In Step 107, the computing device performs a validation process of the first DCN model and the second DCN model by using the plural pieces of validation data obtained in Step 101. That is, the computing device improves the first and second DCN models by inputting the plural pieces of validation data to the first and second DCN models to fine-tune hyperparameters of the first and second DCN models. In an embodiment, the DCN models are validated by using a Tensorflow deep learning framework created by Google, but the disclosure is not limited thereto.

In Step 108, the computing device performs a test process on the first DCN model and the second DCN model that have been improved in Step 107 by using the plural pieces of test data obtained in Step 101. That is, the computing device tests the first and second DCN models with the plural pieces of test data, in order to evaluate performance of the first and second DCN models. In an embodiment, the DCN models are validated also by using the Tensorflow deep learning framework, but the disclosure is not limited thereto.

Figure 3:
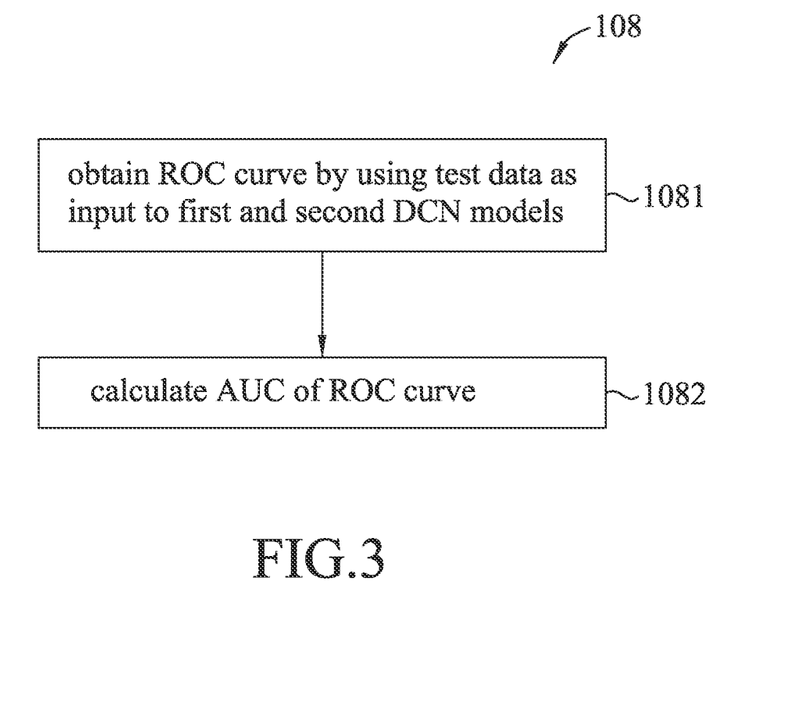
FIG. 3 is a flow chart that exemplarily illustrates sub-steps of Step 108 of FIG. 1 according to an embodiment of the disclosure.

According to some embodiments, Step 108 may include Sub-steps 1081 and 1082 that are shown in FIG. 3. Referring to FIG. 3, in Sub-step 1081, the computing device obtains receiver operating characteristic (ROC) curves respectively of the first DCN model and the second DCN model by using the plural pieces of test data as input to the first and second DCN models. Each ROC curve has points each of which indicates a pair of values, one value being of sensitivity and one value being one minus specificity, and corresponds to a value of a threshold that is associated with the score outputted by the respective one of the first and second DCN models and that is for determining whether a fracture is diagnosed.

In Sub-step 1082, the computing device calculates, for each of the ROC curves, the Area under the Curve (AUC) of the ROC curve for evaluating the performance of the respective one of the first and second DCN models.

According to an embodiment, the computing device may further evaluate in Step 108 (before or after Sub-steps 1081 and 1082) accuracies of fracture localization (with, for example, 95% confidence intervals calculated based on binomial proportion) respectively for the first and second DCN models with respect to the Grad-CAM images outputted by the first and second DCN models, and make the evaluated accuracies secondary endpoints.

Returning to FIG. 1, next, in Step 109, the computing device determines, for each DCN model of the first and second DCN models, a decision threshold for the DCN model by finding one of the points on the ROC curve obtained for the DCN model that results in a maximum value of the Youden index for the ROC curve, which is the point on the ROC curve that has the greatest sum of the sensitivity value and the specificity value among the points on the ROC curve. Then, the first DCN model that has the decision threshold thereof determined may be provided to serve as the fraction-detection tool for detecting overt fracture in the relevant bone in a radiograph, and the second DCN model that has the decision threshold thereof determined may be provided to serve as the fraction-detection tool for detecting occult fracture in the relevant bone.

It should be noted that modifications can be made to the method 100 illustrated in FIG. 1 without going beyond the disclosure. For example, obtaining the plural pieces of validation data and obtaining the plural pieces of test data are not limited to being carried out in step 101. The plural pieces of validation data may be obtained at any time before Step 107, and the plural pieces of test data may be obtained at any time before Step 108. Besides, the validation process, the test process and the determination of the decision threshold for the first DCN model are not limited to being carried out in steps 107, 108 and 109, respectively, and may be performed between Step 104 and Step 105.

Figure 4:
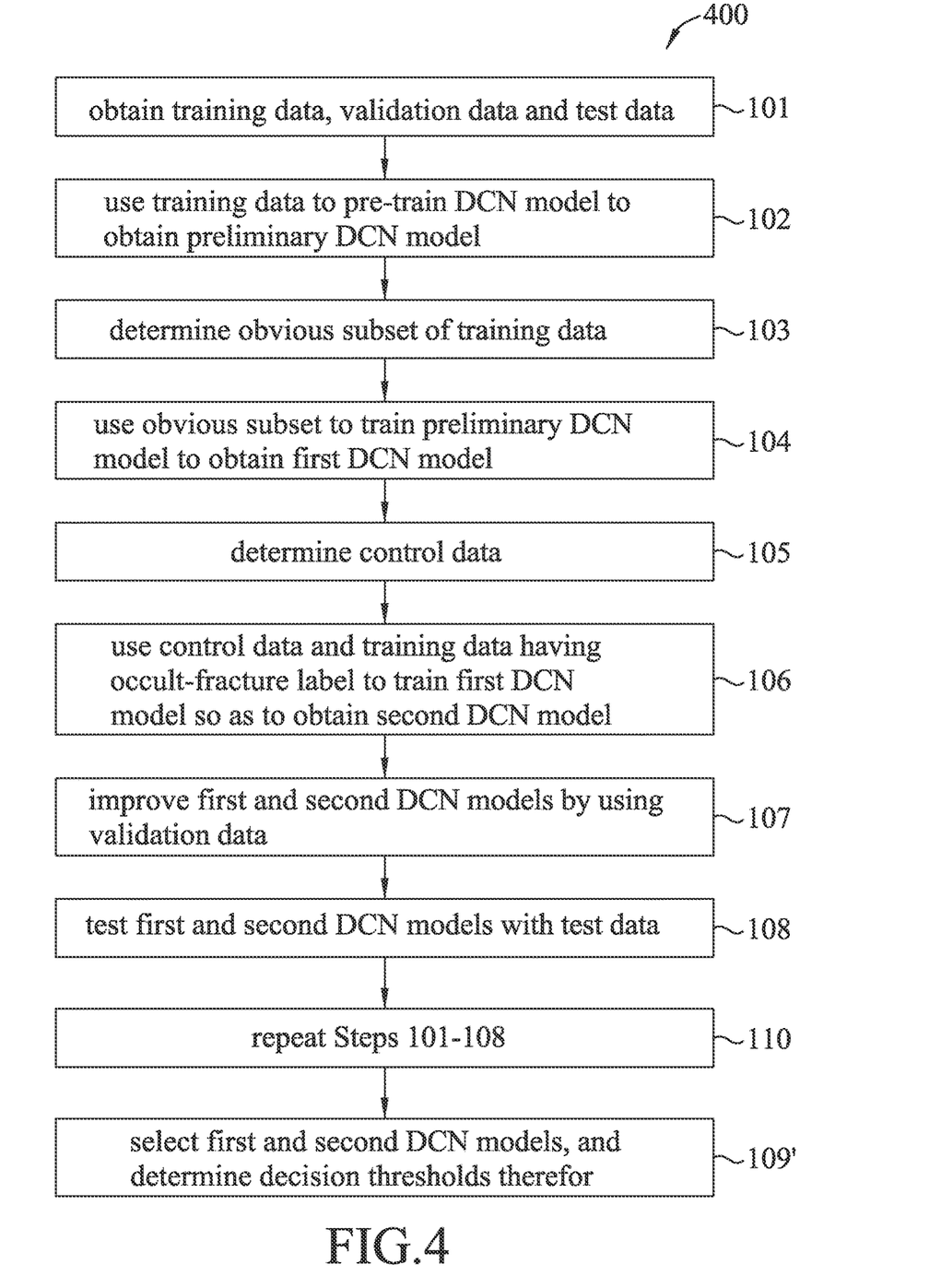
FIG. 4 is a flow chart that exemplarily illustrates another method for providing fracture-detection tools according to an embodiment of the disclosure.

FIG. 4 exemplarily illustrates another method 400 for developing and providing fracture-detection tools based on DCN technique according to an embodiment of the disclosure. The method 400 is similar to the method 100 of FIG. 1, and includes Steps 101-108 that are identical to those of FIG. 1. However, after Step 108, the method 400 goes to Step 110, in which Steps 101-108 are repeated at least one more time, in order to obtain at least one additional first DCN model and at least one additional second DCN model. According to an embodiment, the computing device may repeat Steps 101-108 two more rounds in Step 110. That is, totally three rounds of Steps 101-108 are performed respectively by using three different datasets each including a different plurality of pieces of training data, a different plurality of pieces of validation data and a different plurality of pieces of test data (corresponding to the training radiographs, validation radiographs and test radiographs that are randomly separated in Sub-step 1011 of FIG. 2), in order to respectively obtain three first DCN models, to respectively obtain three second DCN models, to obtain six ROC curves respectively of the three first DCN models and three second DCN models, and to obtain six AUCs respectively for the three first DCN models and three second DCN models.

Next, the process goes to Step 109', in which the computing device selects one of the multiple first DCN models thus obtained (e.g., one of three first DCN models in the case of the three-round scenario) that has the best evaluated performance thereamong, and determines a decision threshold for the first DCN model thus selected, so that the first DCN model thus selected that has the decision threshold thereof determined may be provided to serve as the fraction-detection tool for detecting overt fracture. Also, the computing device selects one of the multiple second DCN models thus obtained (e.g., one of three second DCN models in the case of the three-round scenario) that has the best evaluated performance thereamong, and determines a decision threshold for the second DCN model thus selected, so that the second DCN model thus selected that has the decision threshold thereof determined may be provided to serve as the fraction-detection tool for detecting occult fracture. According to an embodiment, the first and second DCN models may be selected based on the AUCs of the ROC curves thereof. That is, the selected first DCN model may be the first DCN model that has the maximum AUC among the AUCs determined for the first DCN models, and the selected second DCN model may be the second DCN model that has the maximum AUC among the AUCs determined for the second DCN models.

Likewise, decision thresholds of the selected first and second DCN models may be determined based on their Youden indexes as discussed in the above with respect to Step 109 of FIG. 1.

According to some implementations of the disclosure, the two fracture-detection tools (one specialized for overt fracture and the other for occult fracture) that are developed and provided by the method 100 may effectively achieve high accuracy for detecting fractures in scaphoids based on plain hand radiographs, and the repeat and select processes introduced in the method 400 may bring about even higher detection accuracy. Therefore, the present disclosure provides a useful and also economical way to assist physicians in diagnosing fractures, especially in diagnosis concerning occult fractures that used to be not easily detectable from radiographs and that usually lead to misdiagnosis.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A method comprising steps of:
    A) obtaining plural pieces of training data each of which includes a different radiographic image of a bone and has a label indicating one of an overt fracture, an occult fracture and no fracture, wherein the plural pieces of training data include at least one piece of training data each having the label indicating occult fracture;
    B) using the plural pieces of training data to pre-train a deep convolutional network (DCN) model to obtain a preliminary DCN model;
    C) determining a subset of the plural pieces of training data by at least excluding any piece of training data that has the label indicating occult fracture;
    D) using the subset to train the preliminary DCN model to obtain a first DCN model, wherein the first DCN model, when receiving a piece of input data that includes a radiographic image of a bone under examination, outputs a score that indicates probability of overt fracture existing in the radiographic image of the bone under examination;
    E) determining multiple pieces of control data each of which includes a different radiographic image of a bone and, when being inputted to the first DCN model, enables the first DCN model to output a score indicating a probability of overt fracture that is lower than a predetermined threshold; and
    F) using the multiple pieces of control data and said any piece of training data, the label of which indicates occult fracture, that was excluded in step C) to train the first DCN model to obtain a second DCN model, wherein the second DCN model, when receiving another piece of input data that includes a radiographic image of a bone under examination, outputs a score indicating probability of occult fracture existing in the radiographic image.

2. The method of claim 1, wherein step F) is to obtain the second DCN model that, when receiving the another piece of input data, further outputs a gradient-weighted class activation mapping (Grad-CAM) image that indicates a possible site of any fracture that is present in the radiographic image included in the another piece of input data.

3. The method of claim 1, wherein step D) is to obtain the first DCN model that, when receiving the piece of input data, further outputs a gradient-weighted class activation mapping (Grad-CAM) image that indicates a possible site of any fracture that is present in the radiographic image included in the piece of input data.

4. The method of claim 1, wherein step A) is to obtain the plural pieces of training data each including the radiographic image which is a posterior-anterior (PA) scaphoid view.

5. The method of claim 4, wherein step A) includes sub-steps of:
    A-1) obtaining a plurality of radiographs of scaphoids, each of which has been confirmed to show one of an overt fracture, an occult fracture and no fracture; and
    A-2) for each of the plurality of radiographs,
        analyzing the radiograph to define a scaphoid region in the radiograph;
        extracting a portion of the radiograph that contains the scaphoid region; and
        generating one of the plural pieces of training data that corresponds to the radiograph and that includes the portion of the radiograph thus extracted and a label, the portion of the radiograph serving as the radiographic image, the label being set based on which one of an overt fracture, an occult fracture and no fracture the radiograph is confirmed to show.

6. The method of claim 1, wherein:
step A) is to further obtain plural pieces of validation data and plural pieces of test data, each piece of data among the pieces of validation data and the pieces of test data including a different radiographic image of a bone and having a label indicating one of an overt fracture, an occult fracture and no fracture; and
the method further comprising steps of:
G) improving the second DCN model obtained in step F) by inputting the plural pieces of validation data to the second DCN model; and
H) testing the second DCN model that has been improved in step G) with the plural pieces of test data, in order to evaluate performance of the second DCN model.

7. The method of claim 6, wherein step H) includes sub-steps of:
H-1) obtaining a receiver operating characteristic (ROC) curve of the second DCN model by using the plural pieces of test data, the ROC curve having points each of which corresponds to a value of a threshold that is associated with the score outputted by the second DCN model and that is for determining whether a fracture is diagnosed; and
H-2) calculating the Area under the Curve (AUC) of the ROC curve for evaluating the performance of the second DCN model.

8. The method of claim 7, further comprising a step of:
I) determining a decision threshold for the second DCN model by finding one of the points on the ROC curve that results in a maximum value of the Youden index for the ROC curve.

9. The method of claim 7, further comprising steps of:
J) performing steps A) to H) three rounds respectively by using three different datasets each of which includes a different plurality of pieces of training data, a different plurality of pieces of validation data and a different plurality of pieces of test data, in order to respectively obtain three second DCN models; and
K) selecting one of the three second DCN models that has the best evaluated performance thereamong, and determining a decision threshold for the second DCN model thus selected by finding one of the points on the ROC curve of the second DCN model thus selected that results in a maximum value of the Youden index for said ROC curve.

10. The method of claim 1, wherein:
step A) is to further obtain plural pieces of validation data and plural pieces of test data, each piece of data among the pieces of validation data and the pieces of test data including a different radiographic image of a bone and having a label indicating one of an overt fracture, an occult fracture and no fracture; and
the method further comprising steps of:
L) improving the first DCN model obtained in step D) by inputting the plural pieces of validation data to the first DCN model; and
M) testing the first DCN model that has been improved in step L) with the plural pieces of test data, in order to evaluate performance of the first DCN model.

11. The method of claim 10, further comprising steps of:
O) performing steps A) to D), L) and M) three rounds respectively by using three different datasets each of which includes a different plurality of pieces of training data, a different plurality of pieces of validation data and a different plurality of pieces of test data, in order to respectively obtain three first DCN models; and
P) selecting one of the three first DCN models that has the best evaluated performance thereamong, and determining a decision threshold for the first DCN model thus selected by finding one of the points on the ROC curve of the first DCN model thus selected that results in a maximum value of the Youden index for said ROC curve.

12. The method of claim 10, wherein step M) includes sub-steps of:
M-1) obtaining a receiver operating characteristic (ROC) curve of the first DCN model by using the plural pieces of test data, the ROC curve having points each of which corresponds to a value of a threshold that is associated with the score outputted by the first DCN model and that is for determining whether a fracture is diagnosed; and
M-2) calculating the Area under the Curve (AUC) of the ROC curve for evaluating the performance of the first DCN model.

13. The method of claim 12, further comprising a step of:
N) determining a decision threshold for the first DCN model by finding one of the points on the ROC curve that results in a maximum value of the Youden index for the ROC curve.

* * * * *